(12) United States Patent
Ohara et al.

(10) Patent No.: US 6,511,431 B2
(45) Date of Patent: Jan. 28, 2003

(54) RADIAL SCAN, FORWARD VIEWING ULTRASONIC ENDOSCOPE

(75) Inventors: Kenichi Ohara, Gunma (JP); Toshiyuki Hashiyama, Saitama (JP)

(73) Assignee: Pentax Corporation, Tokyo (JP)

( * ) Notice: Subject to any disclaimer, the term of this patent is extended or adjusted under 35 U.S.C. 154(b) by 0 days.

(21) Appl. No.: 09/850,234

(22) Filed: May 8, 2001

(65) Prior Publication Data

US 2001/0041841 A1 Nov. 15, 2001

(30) Foreign Application Priority Data

May 10, 2000 (JP) ..................... 2000-136730
May 10, 2000 (JP) ..................... 2000-136731
May 10, 2000 (JP) ..................... 2000-136732

(51) Int. Cl.[7] ............................... A61B 8/00
(52) U.S. Cl. ................. 600/453; 600/461; 600/459
(58) Field of Search ................ 600/437, 449, 600/447, 459, 460, 461, 462, 463, 453

(56) References Cited

U.S. PATENT DOCUMENTS 5,971,929 A * 10/1999 Sakamoto et al. .......... 600/462
6,095,970 A 8/2000 Hidaka et al.
6,149,598 A * 11/2000 Tanaka ..................... 600/437
6,193,666 B1 * 2/2001 Ouchi ....................... 600/459

FOREIGN PATENT DOCUMENTS

JP 2-265534 10/1990

* cited by examiner

Primary Examiner—Francis J. Jaworski
Assistant Examiner—Maulin Patel
(74) Attorney, Agent, or Firm—Greenblum & Bernstein, P.L.C.

(57) ABSTRACT

In a radial scan, forward viewing ultrasonic endoscope, a plurality of flexible substrates for transmitting signals to and from an ultrasonic probe extend rearward from the ultrasonic probe, a flexible substrate passage hole of an arcuate cross-sectional shape through which the flexible substrates pass is formed in a front end portion body in an axial direction, and the wirings on the flexible substrates are connected to a signal cable passing through the insertion portion of the endoscope.

18 Claims, 11 Drawing Sheets

FIG. 11
FIG. 12
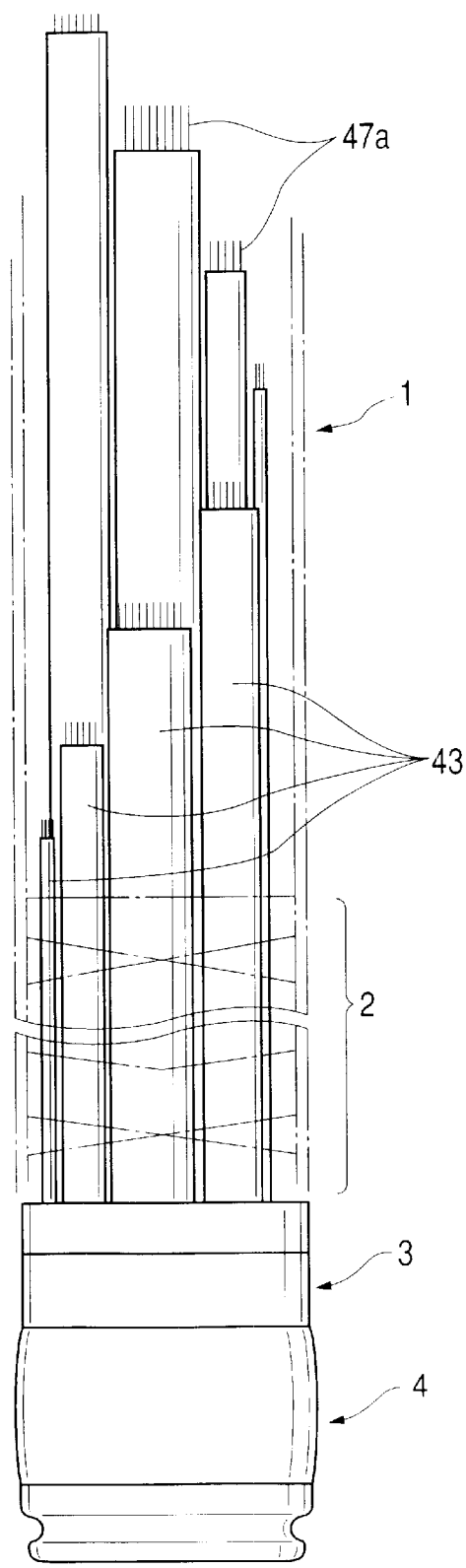
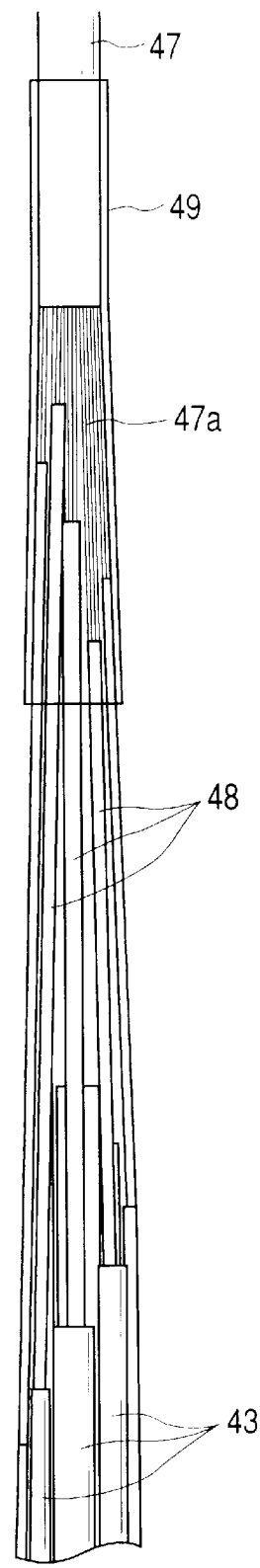

RADIAL SCAN, FORWARD VIEWING ULTRASONIC ENDOSCOPE

BACKGROUND OF THE INVENTION

The present invention relates to a radial scan, forward viewing ultrasonic endoscope having at the tip of an insertion portion objective optics for optical examination of the area ahead of said insertion portion and an ultrasonic probe for performing radial scan by ultrasonic waves.

For ultrasonic endoscopes that can optically examine a body cavity while performing ultrasonic scan, it is generally considered advisable to project ultrasonic waves from the tip of an insertion portion to perform lateral scan as the area which lies the nearest possible to the scanning direction is being examined optically. The ultrasonic endoscopes are structurally designed to meet this requirement.

However, the greatest value of ultrasonic endoscopes lies not in obtaining an ultrasonic cross-sectional image of the other side of an abnormal area of the mucous membrane in the body cavity of interest but rather in inserting the ultrasonic endoscope into an organ adjacent the inaccessible organ and performing ultrasonic scan from that organ.

Therefore, effective ultrasonic scan is inmost cases radial scan about the longitudinal axis of the tip of the insertion portion whereas effective optical examination is forward viewing which is most convenient for checking the area ahead of the insertion portion of the endoscope as it is passed into the body cavity.

However, ultrasonic endoscopes of this type which are commonly called "radial scan, forward viewing ultrasonic endoscopes" have several problems to solve, such as designing a structure that can shorten the rigid tip, and no commercial product has been put on the market.

SUMMARY OF THE INVENTION

An object, therefore, of the present invention is to provide a practically feasible radial scan, forward viewing ultrasonic endoscope that can minimize the length of the rigid tip of the insertion portion.

This object of the invention can be attained by a radial scan, forward viewing ultrasonic endoscope having an ultrasonic probe that is formed in annular shape to permit radial scan and which is provided at the forward end of an insertion portion, and a forward end portion body that is fitted with objective optics for examining the area ahead of the insertion portion and which has a smaller outside diameter in the front half which is fitted into the ultrasonic probe, wherein a plurality of flexible substrates for transmitting signals to and from the ultrasonic probe extend rearward from the ultrasonic probe, a flexible substrate passage hole of an arcuate cross-sectional shape through which the flexible substrates pass is formed in the front end portion body in an axial direction, and the wirings on the flexible substrates are connected to a signal cable passing through the insertion portion.

In a preferred embodiment, at least one area of the flexible substrate passage hole is divided into portions in a circumferential direction. In another preferred embodiment, a nut member for urging and fixing the ultrasonic probe against the front end portion body from the front meshes with the outer circumferential surface of the distal end portion of the front end portion body.

This object of the invention can also be attained by a radial scan, forward viewing ultrasonic endoscope having an ultrasonic probe that is formed in annular shape to permit radial scan and which is provided at the front end of an insertion portion, and a front end portion body that is fitted with objective optics for examining the area ahead of the insertion portion and which has a smaller outside diameter in the front half which is fitted into the ultrasonic probe, wherein a plurality of flexible substrates for transmitting signals to and from the ultrasonic probe are arranged in arcs around the longitudinal axis of the ultrasonic probe and allowed to pass through the front end portion body and a rotation preventing member for preventing relative rotation of the ultrasonic probe and the front end portion body around the longitudinal axis is provided in a position in that area of a circumferential extension of the series of arcs where no flexible substrate is provided.

In a preferred embodiment, the rotation preventing member is independent of both the ultrasonic probe and the forward end portion body and a groove into which the rotation preventing member is to be fitted is formed in each of the ultrasonic probe and the front end portion body.

This object of the invention can also be attained by a radial scan, forward viewing ultrasonic endoscope having an ultrasonic probe that is formed in annular shape to permit radial scan and which is provided at the front end of an insertion portion, a front end portion body that is fitted with objective optics for examining the area ahead of the insertion portion and which has a smaller outside diameter in the front half which is fitted into the ultrasonic probe, and an inflatable balloon provided to surround the ultrasonic probe, wherein a plurality of flexible substrates for transmitting signals to and from the ultrasonic probe are arranged in arcs around the longitudinal axis of the ultrasonic probe and allowed to pass through the front end portion body and fluid channels that communicate into the balloon are provided in a position in that area of a circumferential extension of the series of arcs where no flexible substrate is provided.

The present disclosure relates to the subject matter contained in Japanese patent application Nos. 2000-136730, 2000-136731 and 2000-136732 (all filed on May 10, 2000), which are expressly incorporated herein by reference in their entireties.

BRIEF DESCRIPTION OF THE DRAWINGS

FIG. 11 is a schematic view showing a state of backward end portions of the flexible substrates in the embodiment of the present invention.

FIG. 12 is a side view of portions of connection of the flexible substrates to a signal cable in the embodiment of the present invention.

DESCRIPTION OF THE PREFERRED EMBODIMENT

An embodiment of the present invention will be described below with reference to the accompanied drawings.

Figure 2:
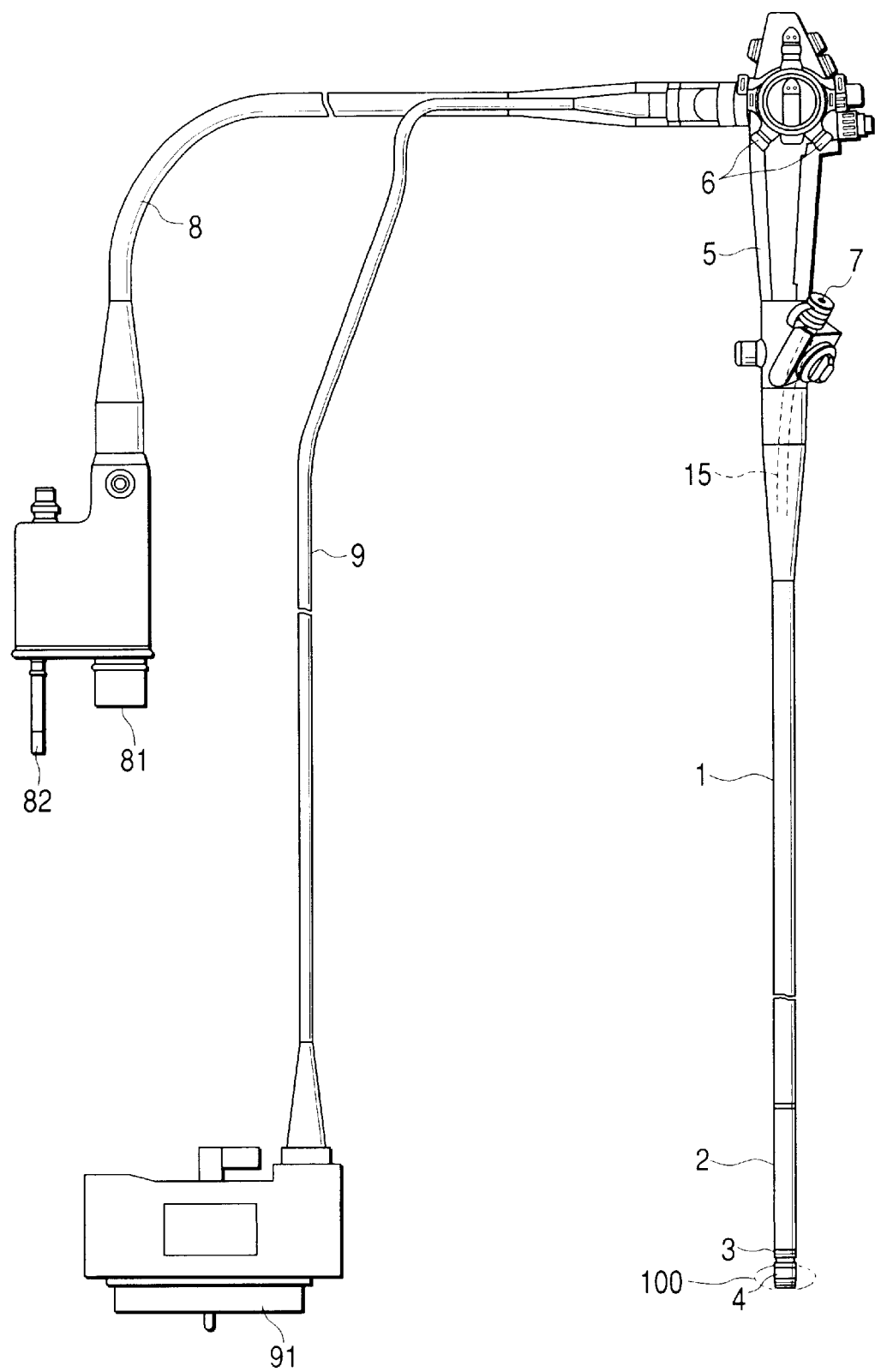
FIG. 2 is a side view showing the overall configuration of the ultrasonic endoscope according to the embodiment of the present invention.

FIG. 2 shows a radial scan, forward viewing ultrasonic endoscope which comprises a flexible tube portion 1 to be inserted into a body cavity, a curved portion 2 which is bent by remote control being connected to a forward end of the flexible tube portion 1, a forward-end-portion body 3 connected to a forward end of the curved portion 2, and an ultrasonic probe 4 attached to the forward-end-portion body 3. The reference numeral 100 designates an inflatable/deflatable balloon which is detachably provided to surround the ultrasonic probe 4.

A curved portion operation knob 6, or the like, for driving the curved portion 2 to bend is disposed in an operation portion 5 connected to a base end of the flexible tube portion 1. The reference numeral 7 designates a treating tool insertion hole through which a treating tool, or the like, is inserted into a treating tool-pass channel 15 disposed in the flexible tube portion 1 so as to be inserted into the flexible tube portion 1.

A video signal connector portion 81 to be connected to a video processor not shown and a light guide connector portion 82 are provided side by side at a forward end of a first connection flexible tube 8 connected to the operation portion 5. An ultrasonic signal connector portion 91 to be connected to an ultrasonic signal processor not shown is provided at a forward end of a second connection flexible tube 9.

Figure 1:
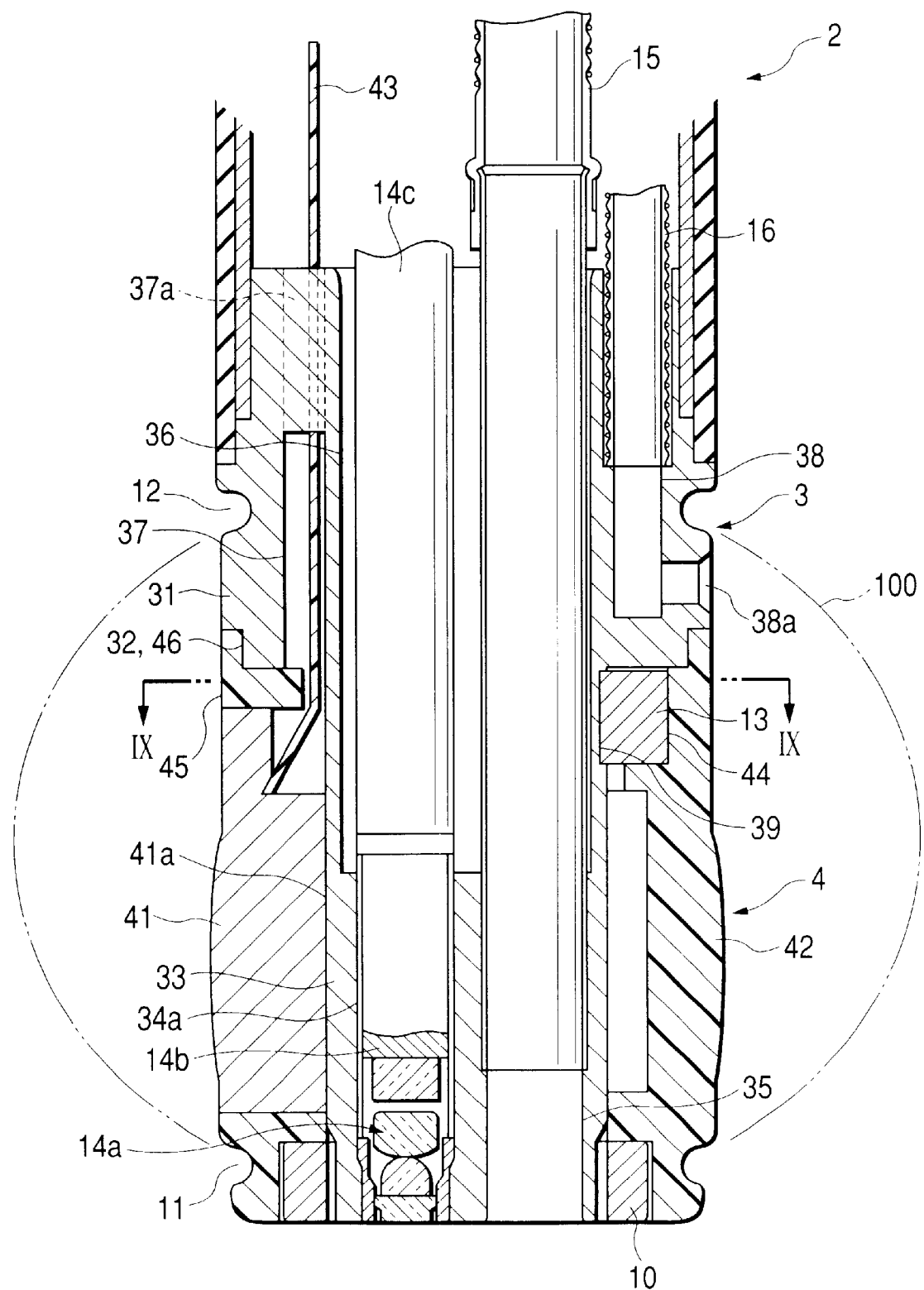
FIG. 1 is a side sectional view of a forward end portion of an insertion portion of an ultrasonic endoscope according to an embodiment of the present invention.

FIG. 1 shows a forward end portion of an insertion portion in which the ultrasonic probe 4 includes an ultrasonic vibrator arrangement portion 41 formed approximately annularly, and a plastic receptacle member 42 for holding the ultrasonic vibrator arrangement portion 41. The ultrasonic vibrator arrangement portion 41 and the receptacle member 42 are integrated into one unit shown in FIG. 3.

Figure 3:
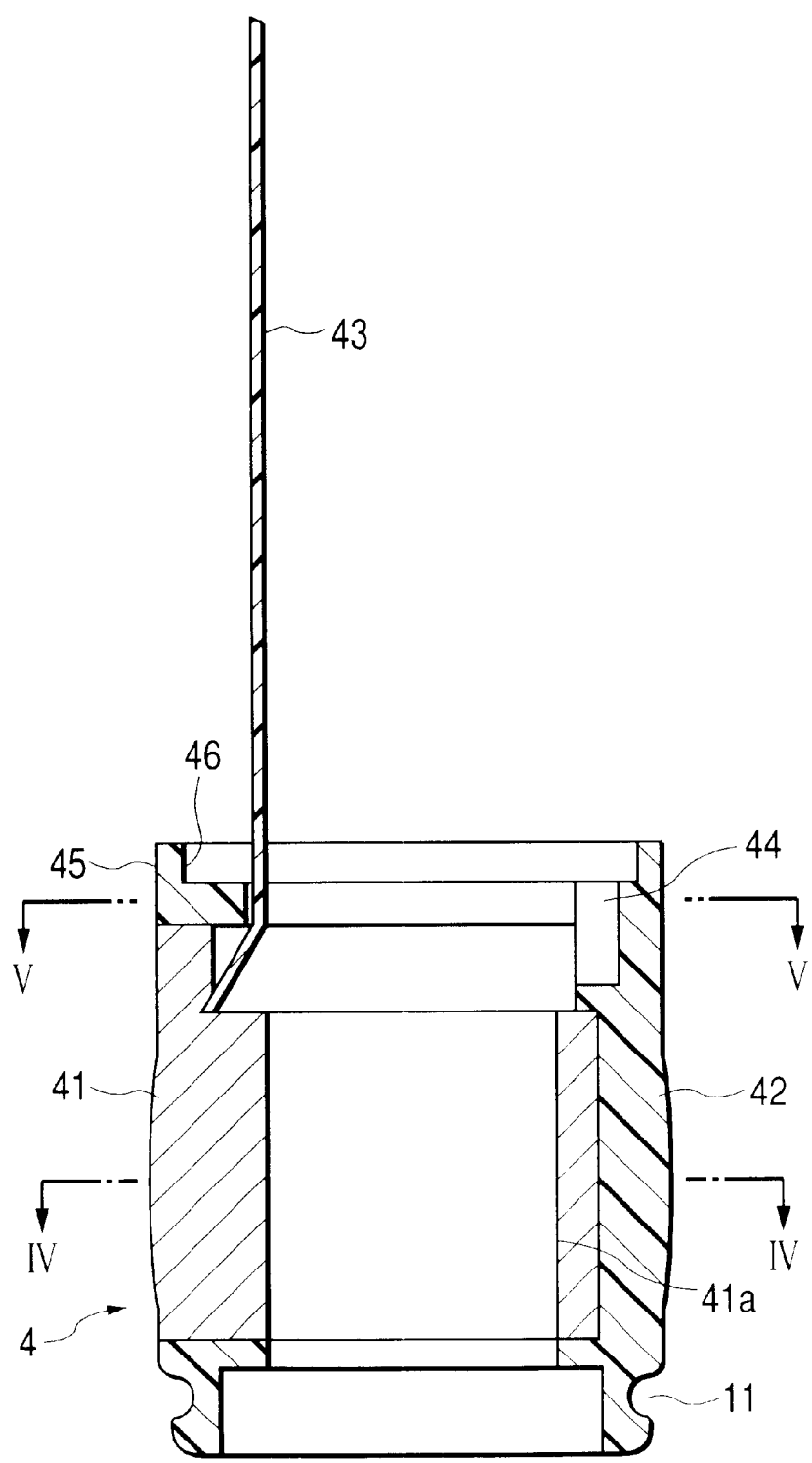
FIG. 3 is a side sectional view of the ultrasonic endoscope according to the embodiment of the present invention.
Figure 4:
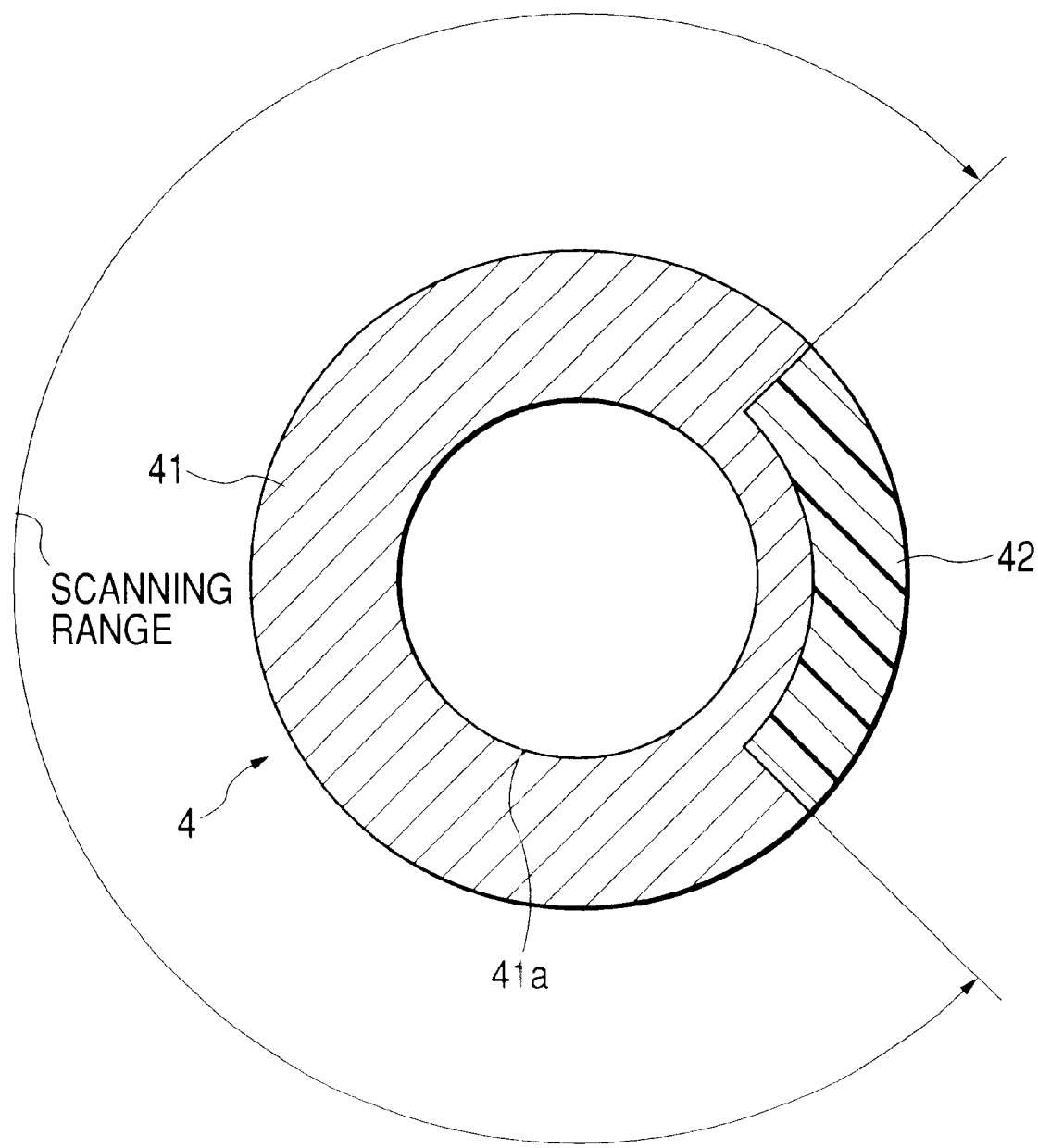
FIG. 4 is a sectional view taken along the line IV—IV in FIG. 3, showing the embodiment of the present invention.

As shown in FIG. 4 which is a sectional view taken along the line IV—IV in FIG. 3, ultrasonic signals are transmitted/received (electronically scanned) successively in a range, for example, of 270°, around an axial line from the ultrasonic vibrator arrangement portion 41 having a large number of ultrasonic vibrators arranged around the axial line. Thus, radial scanning is performed in a direction perpendicular to the axial line.

The inner space of the ultrasonic vibrator arrangement portion 41 is shaped like a cylindrical hole with the axial line as its center. Flexible substrates 43 having wiring for transmitting a signal input into/output from the ultrasonic vibrator arrangement portion 41 are connected to a backward end portion (an upper portion in FIG. 3) of the ultrasonic vibrator arrangement portion 41 so as to extend backward.

Figure 5:
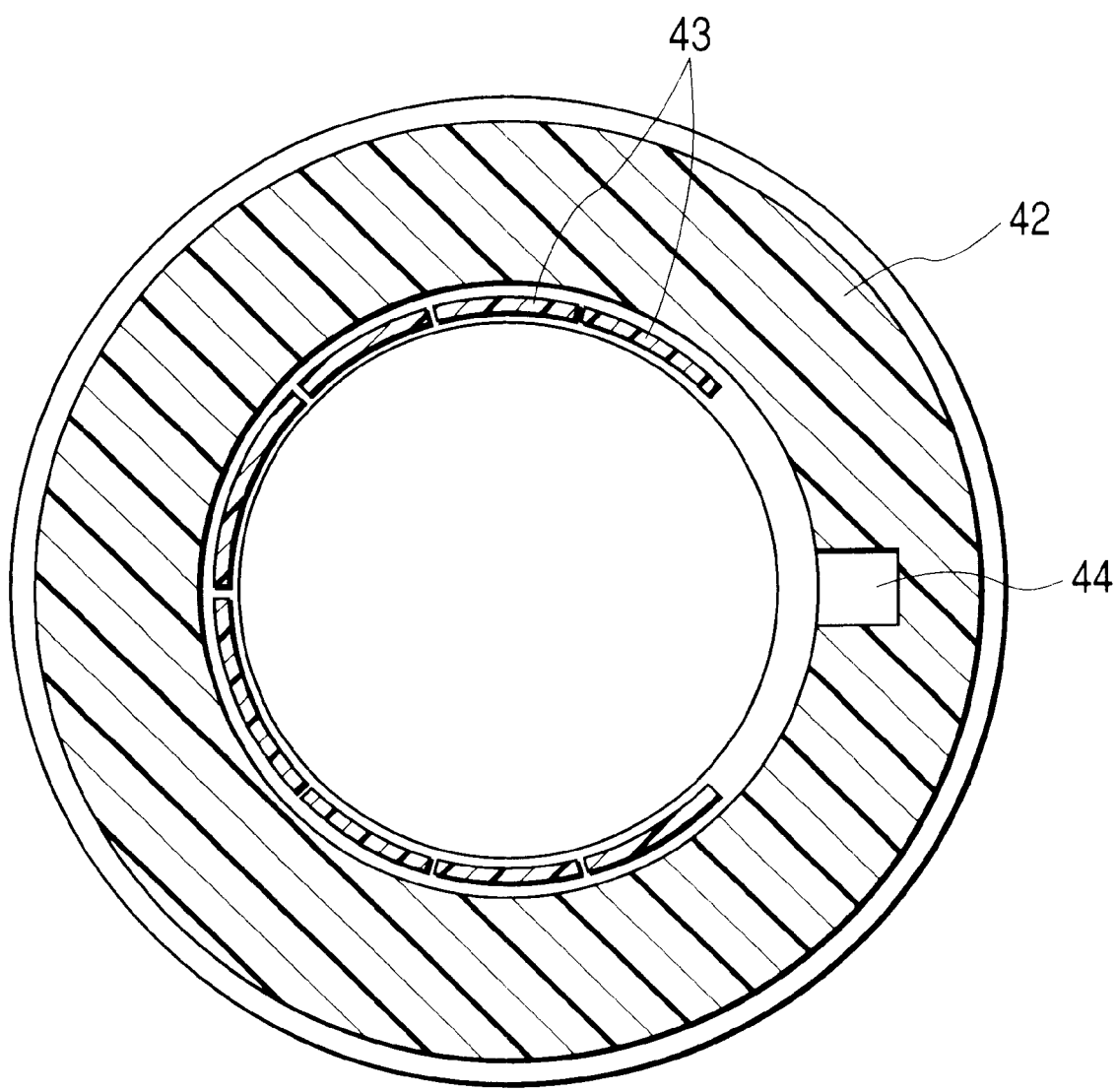
FIG. 5 is a sectional view taken along the line V—V in FIG. 3, showing the embodiment of the present invention.

As shown in FIG. 5 which is a sectional view taken along the line V—V in FIG. 3, the flexible substrates 43 are provided as a plurality of flexible substrates 43 (for example, eight flexible substrates 43), which are provided side by side so as to be shaped like a circular arc around the axial line of the ultrasonic probe 4.

As shown in FIG. 5, the flexible substrates 43 are arranged like a circular arc, for example, in a range of about 270°.

A slot 44 for embedding a rotation stopper member 13 which will be described later is formed in a portion which is extension of the circular arc where the flexible substrates 43 are arranged and which has no arrangement of the flexible substrates 43.

Referring back to FIG. 3, a centering fitting portion 46 to be fitted to a centering fitting portion 32 (which will be described later) of the forward-end-portion body 3 is formed in a backward end portion of the receptacle member 42 so as to be concentric with an outer cirumferential surface (an outer circumferential surface of a boundary portion adjacent to the outer surface of the forward-end-portion body 3) 45 in high dimensional accuracy. A circumferential groove 11 for fixing a forward end portion of the inflatable/deflatable balloon 100 by a belt is formed in a forward end portion of the outer circumferential surface of the receptacle member 42.

Figure 6:
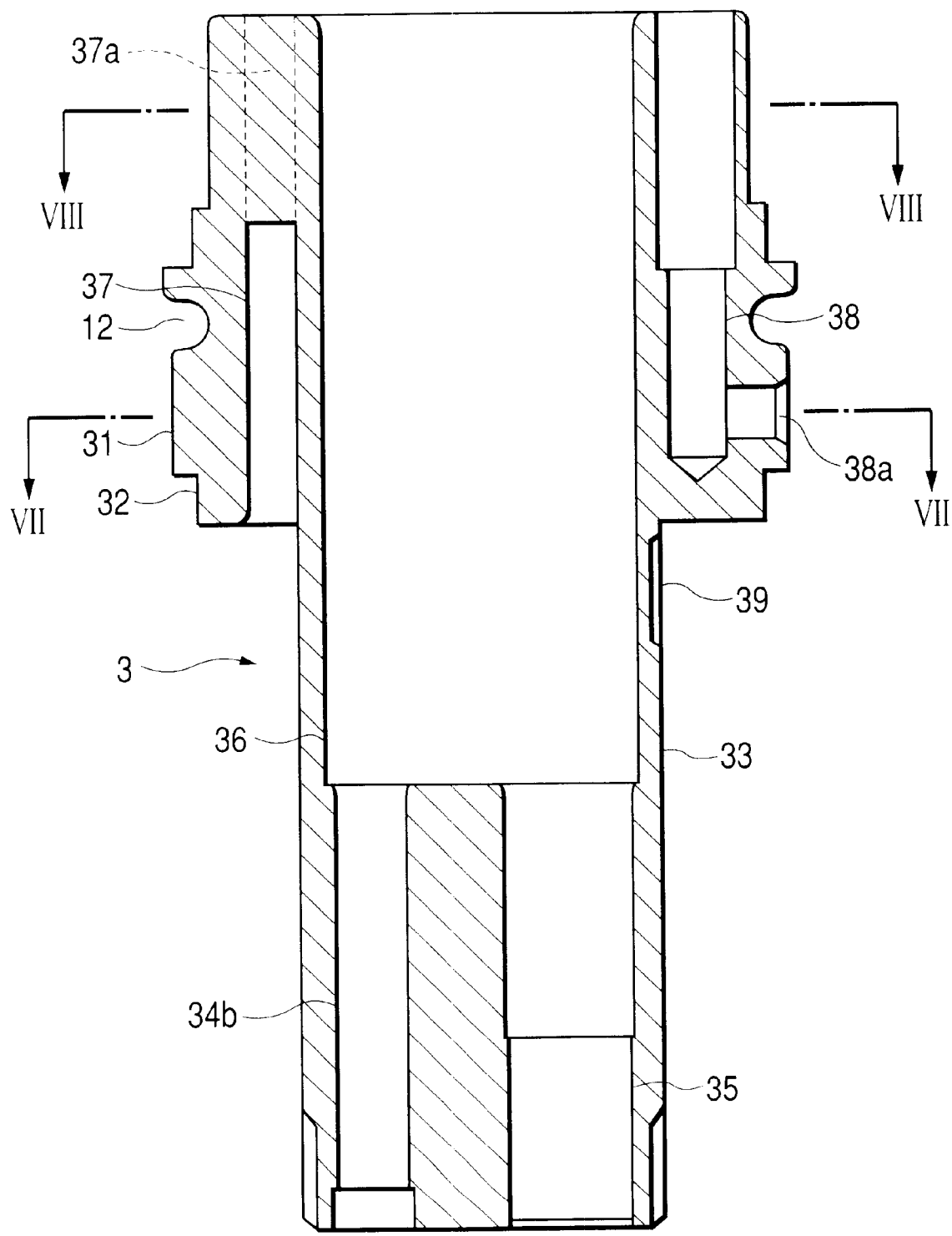
FIG. 6 is a side sectional view of a forward-end-portion body in the embodiment of the present invention.

Referring back to FIG. 1 again, the forward-end-portion body 3 made of a plastic material, or the like, has a forward half portion 33 which is so small in size as to be inserted into an inner circumferential surface 41a of the ultrasonic vibrator arrangement portion 41 of the ultrasonic probe 4 as a single part state of the forward-end-portion body 3 as shown in FIG. 6. Further, an outer circumferential surface 31 of a boundary portion adjacent to the outer circumferential surface of the ultrasonic probe 4 is formed to have the same size as that of the outer circumferential surface 45 of the boundary portion of the ultrasonic probe 4.

A self-aligning fitting portion 32 to be fitted to a self-aligning fitting portion 46 of the ultrasonic probe 4 is formed in a forward end portion of the outer circumferential surface 31 of the boundary portion of the forward-end-portion body 3 so as to be aligned with the outer circumferential surface 31 of the boundary portion in high dimensional accuracy. Further, a circumferential groove 12 for fixing a rear end portion of the balloon 100 by a belt is formed at a backward end of the outer circumferential surface.

An objective arrangement hole 34a, an illumination light guide arrangement hole 34b and a treating tool-pass hole 35 are formed in a forward portion of the forward half portion 33 of the forward-end-portion body 3 so as to be parallel to the axial 25 line. An inclusion-pass hole 36 having an inner diameter slightly smaller than the outer diameter of the forward half portion 33 is formed on the back of the forward portion of the forward half portion 33 so as to extend to a backward end of the forward-end-portion body 3.

Figure 7:
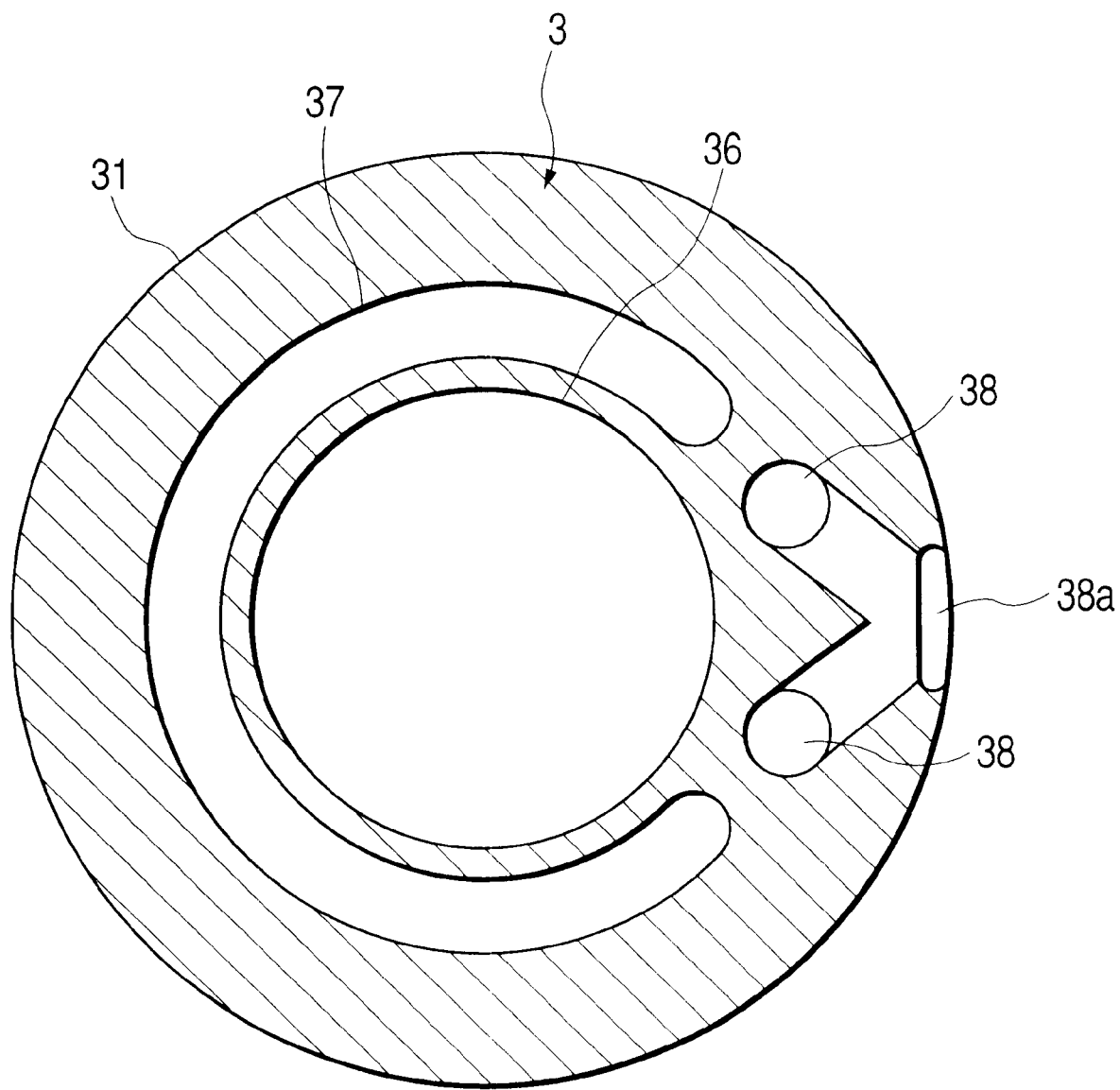
FIG. 7 is a sectional view taken along the line VII—VII in FIG. 6, showing the embodiment of the present invention.

As shown also in FIG. 7 which is a sectional view taken along the line VII—VII in FIG. 6, a flexible substrate-pass hole 37 for making the flexible substrates 43 pass therethrough is formed in a backward half portion of the forward-end-portion body 3 and approximately on a position of extension of the outer circumferential surface of the forward half portion 33 so as to be shaped like a circular arc around the axial line in accordance with the positions of arrangement of the flexible substrates 43.

Figure 8:
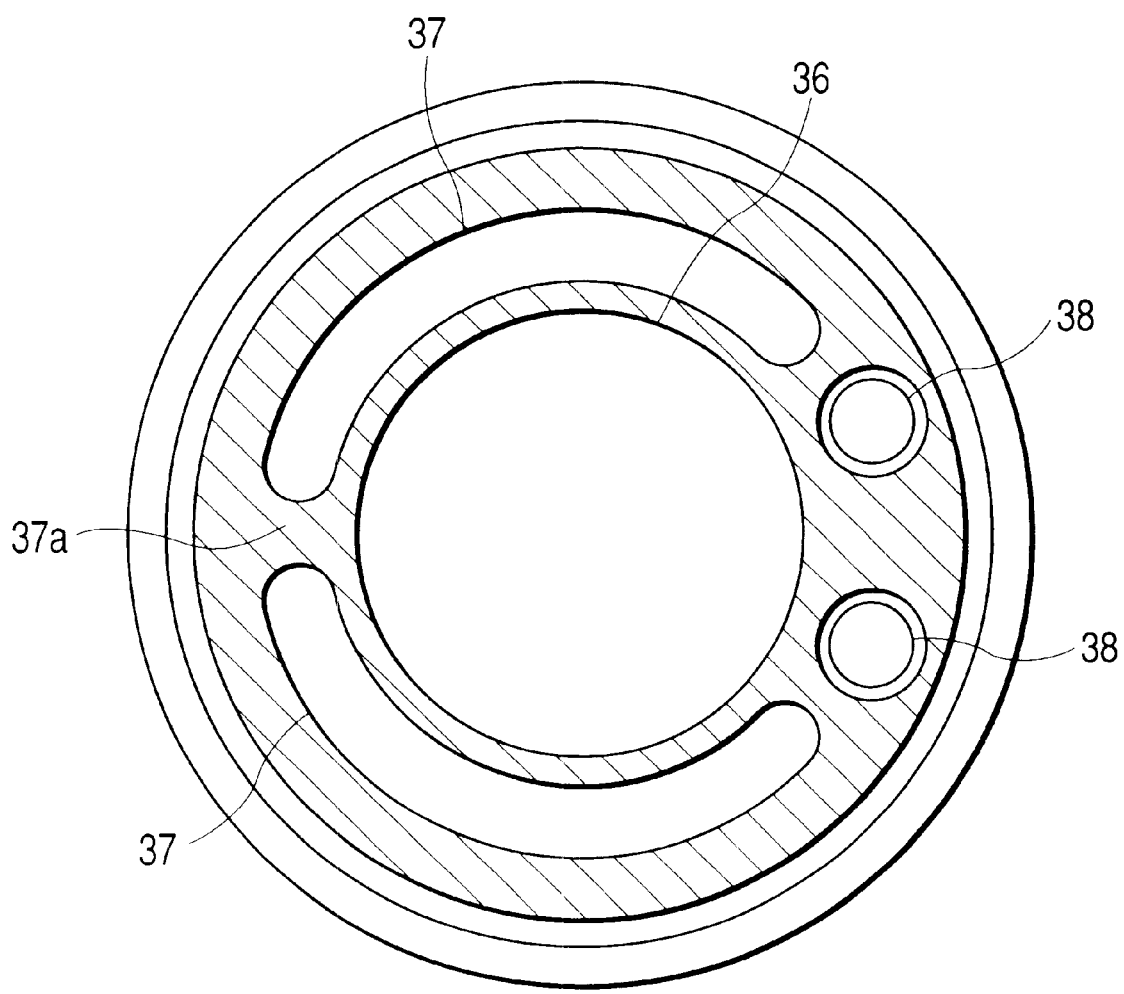
FIG. 8 is a sectional view taken along the line VIII—VIII in FIG. 6, showing the embodiment of the present invention.

Incidentally, as shown in FIG. 8 which is a sectional view taken along the line VIII—VIII in FIG. 6, at least one junction 37a is formed in the middle of the flexible substrate pass hole 37 in the vicinity of the backward end portion of the forward-end-portion body 3 so that the flexible substrate-pass hole 37 is divided into two by the junction 37a to thereby ensure strength sufficient to prevent the forward-end-portion body 3 from being squashed by external force.

Referring back to FIGS. 6 and 7, the flexible substrate-pass hole 37 is shaped like a circular arc in a range of about 280°. Fluid passages 38 for injecting degassing water into the balloon 100 and discharging degassing water from the balloon 100 respectively are formed in a portion in which the flexible substrate-pass hole 37 is not formed. The fluid passages 38 are formed in parallel to the axial line so as to communicate with a balloon communication opening 38a opened into the balloon 100.

The two fluid passages 38 are formed side by side. One of the two fluid passages 38 is used for discharging degassing water and gas. Although the fluid passages 38 do not appear in FIG. 6 (and in FIG. 1) originally, the fluid passages 38 are shown in FIG. 6 (and in FIG. 1) to facilitate an understanding of the description. The reference numeral 39 designates a slot 69 for embedding a rotation stopper member 13.

Referring back to FIG. 1, the ultrasonic probe 4 fitted to the forward half portion 33 of the forward-end-portion body 3 is pressed and fixed to an intermediate stepped surface of the forward-end-portion body 3 by a nut member 10 to be thread-engaged with a male screw formed on the outer circumference of the forward end portion of the forward-end-portion body 3.

Figure 9:
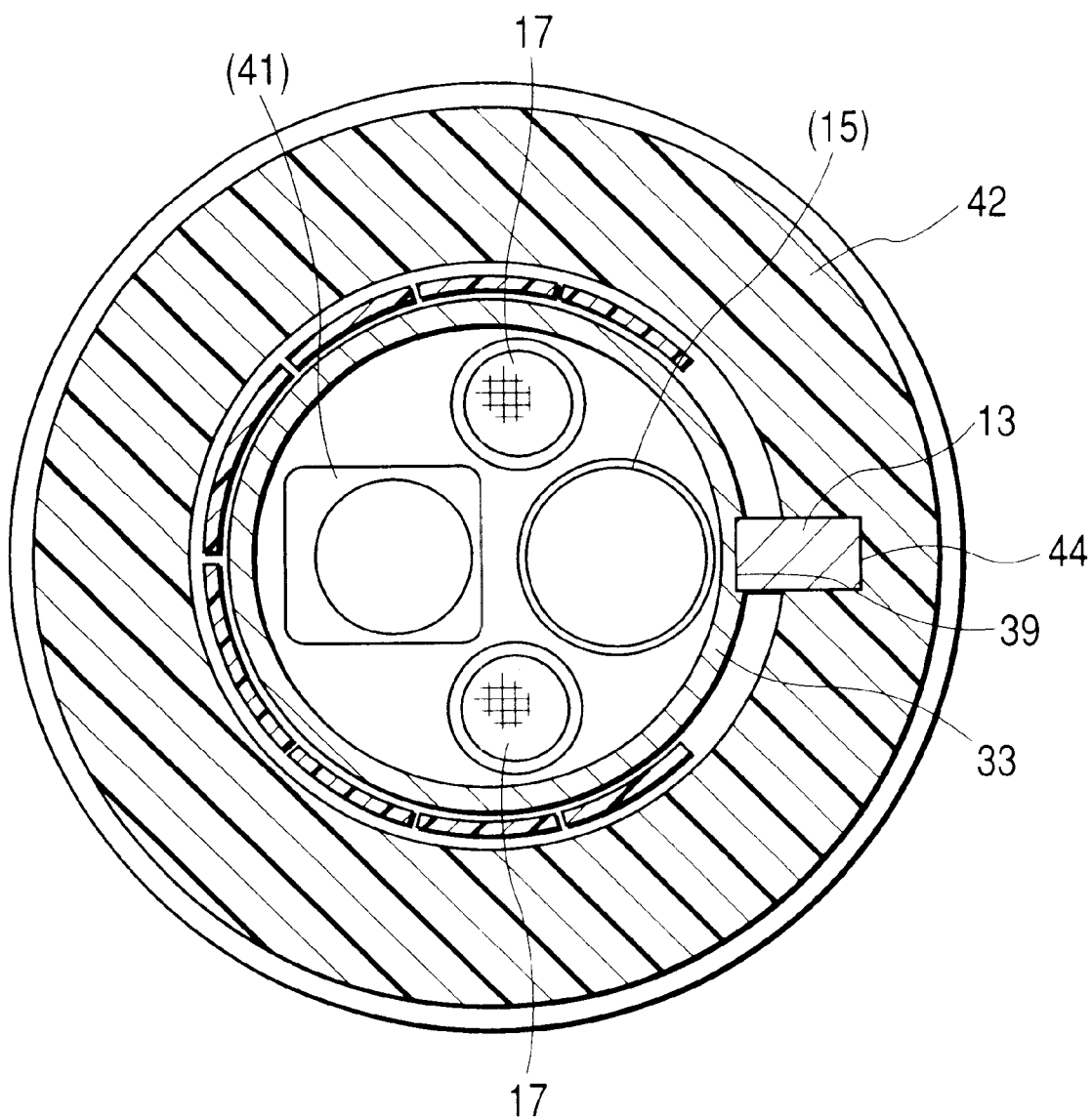
FIG. 9 is a sectional view taken along the line IX—IX in FIG. 1, showing the embodiment of the present invention.

As shown also in FIG. 9 which is a sectional view taken along the line IX—IX in FIG. 1, the rotation stopper member 13 shaped like a rectangular parallelepiped is embedded in the slot 44 of the ultrasonic probe 4 and in the slot 39 of the forward-end portion-body 3 to thereby limit positioning in the direction of rotation of the ultrasonic probe 4 relative to the forward-end-portion body 3. Hence, the relation between the direction of ultrasonic scanning and the direction of observation view field is set correctly. The reference numeral 17 designates illumination light guide fibers.

Referring back to FIG. 1 again, in the state where the ultrasonic probe 4 is fixed to the forward-end-portion body 3, the forward half portion 33 of the forward-end-portion body 3 and the inner circumferential surface 41a of the ultrasonic vibrator arrangement portion 41 are fitted to each other and the centering fitting portion 32 of the forward-end-portion body 3 and the centering fitting portion 46 of the ultrasonic probe 4 are fitted to each other. The gap between the former fitting portions is formed so as to be larger than the gap between the latter fitting portions.

As a result, it is seldom that there occurs a difference in level in the joint portion which is one of joint portions between the forward-end-portion body 3 and the ultrasonic probe 4 and which is between the boundary portion outer circumferential surface 31 of the forward-end-portion body 3 and the boundary portion outer circumferential surface 45 of the ultrasonic probe 4. Thus, a forward end portion having a good property for insertion into a patient is formed.

An objective optical system 14a is disposed in a forward portion of the objective arrangement hole 34. A solid image-pickup device 14b is disposed in a backward portion of the objective arrangement hole 34. A signal cable 14c for transmitting an image-pickup signal, or the like, passes through the inside of the inclusion-pass hole 36 and extends backward into the curved portion 2. A treating tool insertion channel 15 is connected to the treating tool-pass hole 35 through a stainless steel pipe.

Flexible piping tubes 16 are connected to the two fluid passages 38 respectively. The balloon 100 has opposite ends fixed to the circumferential grooves 11 and 12 respectively. Hence, degassing water can be injected into the balloon 100 and discharged from the balloon 100 through the piping tubes 16 by control from the operation portion 5 so that the balloon 100 can be inflated/deflated.

As shown in FIG. 1, the flexible substrates 43 for transmitting a signal inputted into or outputted from the ultrasonic vibrator arrangement portion 41 are drawn backward into the curved portion 2 via the flexible substrate-pass hole 37 formed in the forward-end-portion body 3.

Figure 10:
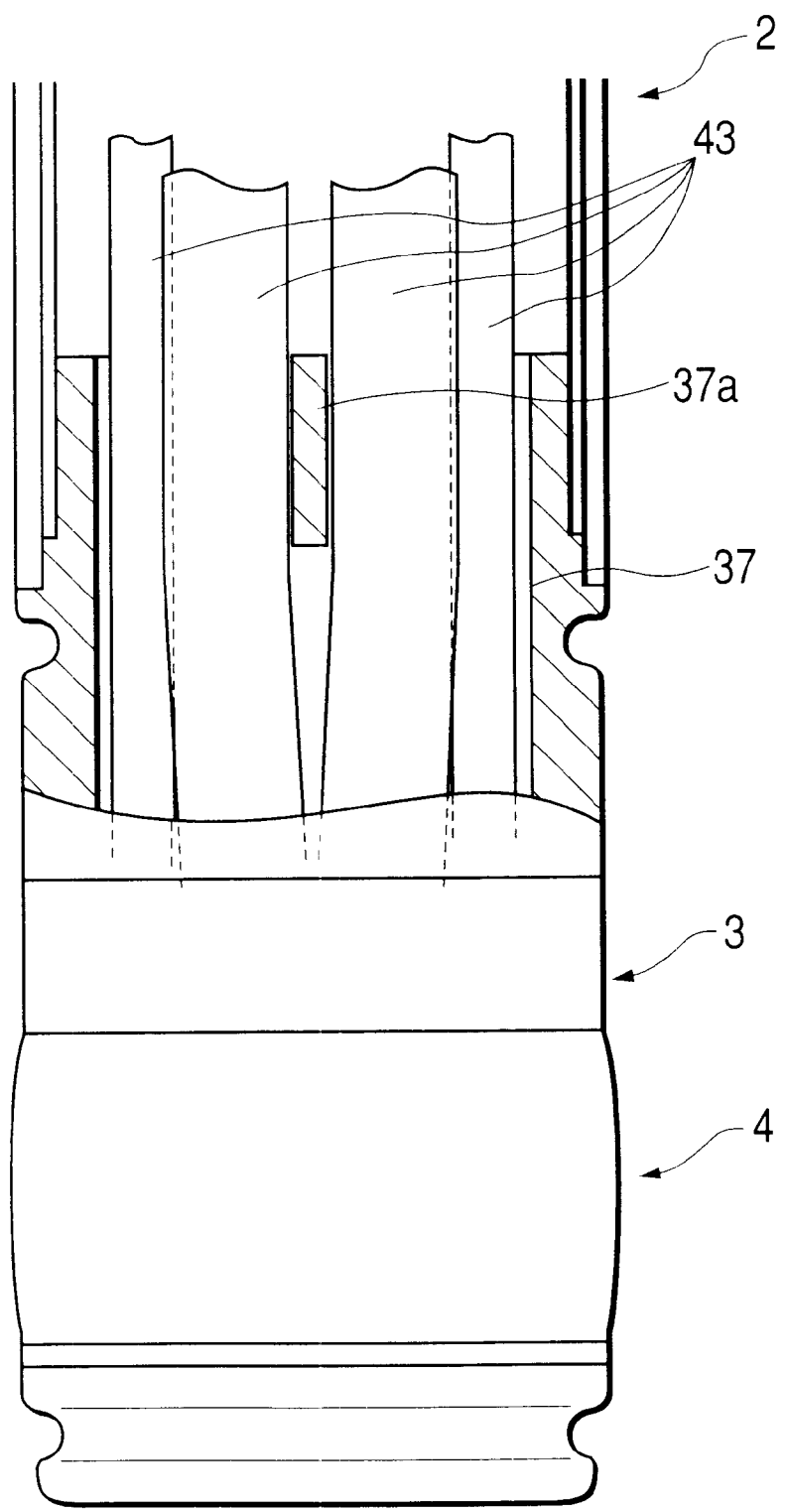
FIG. 10 is a partly sectional view showing a state of passage of flexible substrates in the embodiment of the present invention.

As shown in FIG. 10, in the backward half portion of the flexible substrate-pass hole 37, the flexible substrates 43 are disposed so that the flexible substrates 43 are drawn backward into the curved portion 2 while adjacent flexible substrates 43 slightly overlap each other in order to avoid interference with the junction 37a.

In the curved portion 2, all the signals inputted into or outputted from the ultrasonic vibrator arrangement portion 41 are transmitted by wiring formed in the thin flexible substrates 43. Hence, a signal cable, or the like, need not be inserted/disposed in the curved portion 2.

The flexible substrates 43 are arranged like a circular arc surrounding various inclusions such as the signal cable 14c of the solid image-pickup device 14b, the treating tool insertion channel 15 and the light guide fibers 17. Hence, various inclusions are inserted/disposed in the curved portion 2 without any wasteful inner space, so that the curved portion 2 can be formed so as to be small in size.

As shown in FIG. 11, the flexible substrates 43 are formed to have different lengths respectively. Even the shortest flexible substrate 43 is set to have a length sufficient to pass through the inside of the curved portion 2. The signal cable 47 inserted/disposed in the flexible tube portion 1 has signal wires 47a. The flexible substrates 43 are connected to forward ends of the signal wires 47a respectively while the flexible substrates 43 are displaced successively in the direction of the length of the signal cable 47.

Portions of connection of the flexible substrates 43 to the signal wires 47a of the signal cable 47 are enlarged in diameter by soldering, or the like. Local enlargement can be, however, avoided totally because the portions are displaced successively. Hence, the flexible tube portion 1 and the curved portion 2 can be formed to be small in size.

FIG. 12 shows such connection portions disposed in the inside of the flexible tube portion 1. A forward end portion of the signal cable 47 having a large number of signal wires 47a bound into one is disentangled into individual signal wires 47a in the inside of the flexible tube portion 1. Groups of signal wires 47a which are to be connected to corresponding flexible substrates 43. Each group of signal wires 47a are covered with a flexible heat-shrinkable tube 48 and bundled into one. Such configuration has a good effect on preventing the respective signal wires 47a from being broken.

The respective heat-shrinkable tubes 48 are disposed while end portions of the heat-shrinkable tubes 48 are displaced successively. Hence, the flexibility of the flexible tube portion 1 does not change rapidly, so that the change of the diameter of the flexible tube portion as a whole is smoothened to thereby avoid the enlargement of the diameter. Further, the respective end portions of the heat-shrinkable tubes 48 are covered with a flexible large-diameter heat-shrinkable tube 49 so that the respective end portions are bound into one as a whole.

According to the invention, a plurality of flexible substrates are used as members for transmitting signals to and from the ultrasonic probe, and a flexible substrate passage hole of an arcuate cross-sectional shape is formed in the front end portion body fitted with objective optics and other functional components. As a result, the ultrasonic probe and the front end portion body can be coupled by a simple structural design without producing any steps and the rigid front end of the insertion portion is made as short as possible to fabricate an easily insertable and, hence, practically feasible radial scan, forward viewing ultrasonic endoscope.

According to the invention, a plurality of flexible substrates for transmitting signals to and from the ultrasonic probe are arranged in arcs around the longitudinal axis of the ultrasonic probe and allowed to pass through the front end portion body, and a rotation preventing member for preventing relative rotation of the ultrasonic probe and the front end portion body around the longitudinal axis is provided in a position in that area of a circumferential extension of the series of arcs where no flexible substrate is provided. As a result, the ultrasonic probe and the front end portion body can be coupled by a simple structural design without producing any steps and the rigid front end of the insertion portion is made as short as possible to fabricate an easily insertable and, hence, practically feasible radial scan, forward viewing ultrasonic endoscope.

According to the invention, a plurality of flexible substrates for transmitting signals to and from the ultrasonic probe are arranged in arcs around the longitudinal axis of the ultrasonic probe and allowed to pass through the front end portion body and fluid channels that communicate into the balloon are provided in a position in that area of a circumferential extension of the series of arcs where no flexible substrate is provided. As a result, the ultrasonic probe and the tip body can be coupled by a simple structural design without producing any steps and the rigid front end of the insertion portion is made as short as possible to fabricate an easily insertable and, hence, practically feasible radial scan, forward viewing ultrasonic endoscope.

What is claimed is:

1. A radial scan, forward viewing ultrasonic endoscope having an ultrasonic probe that is formed in annular shape to permit radial scan and which is provided at the front end of an insertion portion, and a front end portion body that is fitted with objective optics for examining the area ahead of said insertion portion and which has a smaller outside diameter in the front half which is fitted into said ultrasonic probe, wherein a plurality of flexible substrates for transmitting signals to and from said ultrasonic probe extend rearward from said ultrasonic probe, a flexible substrate passage hole of an arcuate cross-sectional shape through which said flexible substrates pass is formed in said front end portion body in an axial direction, and the wirings on said flexible substrates are connected to a signal cable passing through said insertion portion.

2. The radial scan, forward viewing ultrasonic endoscope according to claim 1, wherein at least one area of said flexible substrate passage hole is divided into portions in a circumferential direction.

3. The radial scan, forward viewing ultrasonic endoscope according to claim 1, wherein a nut member for urging and fixing said ultrasonic probe against said front end portion body from the front meshes with the outer circumferential surface of the distal end portion of said front end portion body.

4. A radial scan, forward viewing ultrasonic endoscope having an ultrasonic probe that is formed in annular shape to permit radial scan and which is provided at the front end of an insertion portion, and a front end portion body that is fitted with objective optics for examining the area ahead of said insertion portion and which has a smaller outside diameter in the front half which is fitted into said ultrasonic probe, wherein a plurality of flexible substrates for transmitting signals to and from said ultrasonic probe are arranged in arcs around the longitudinal axis of said ultrasonic probe and allowed to pass through said front end portion body and a rotation preventing member for preventing relative rotation of said ultrasonic probe and said front end portion body around the longitudinal axis is provided in a position in that area of a circumferential extension of the series of arcs where no flexible substrate is provided.

5. The radial scan, forward viewing ultrasonic endoscope according to claim 4, wherein said rotation preventing member is independent of both said ultrasonic probe and said front end portion body, and a groove into which said rotation preventing member is to be fitted is formed in each of said ultrasonic probe and said tip body.

6. A radial scan, forward viewing ultrasonic endoscope having an ultrasonic probe that is formed in annular shape to permit radial scan and which is provided at the front end of an insertion portion, a front end portion body that is fitted with objective optics for examining the area ahead of said insertion portion and which has a smaller outside diameter in the front half which is fitted into said ultrasonic probe, and an inflatable balloon provided to surround said ultrasonic probe, wherein a plurality of flexible substrates for transmitting signals to and from said ultrasonic probe are arranged in arcs around the longitudinal axis of said ultrasonic probe and allowed to pass through said front end portion body, and fluid channels that communicate into said balloon are provided in a position in that area of a circumferential extension of the series of arcs where no flexible substrate is provided.

7. An ultrasonic endoscope comprising:
   a flexible tube portion;
   a forward end portion body having an ultrasonic probe and connected to the flexible tube portion; and a plurality of flexible substrates, extending from the forward end portion body to the flexible tube portion, for signal transmission to and from the ultrasonic probe, wherein the flexible substrates are arranged to pass through a predetermined first circumferential area of the forward end portion body, and to define a second circumferential area thereof, where no flexible substrate is provided.

8. The ultrasonic endoscope according to claim 7, wherein the forward end portion body has an arcuate groove for defining the first circumferential area, and the flexible substrates pass through the arcuate groove.

9. The ultrasonic endoscope according to claim 7, further comprising:
   a rotation preventing member, disposed in the second circumferential area, for preventing relative rotation between the forward end portion body and the ultrasonic probe.

10. The ultrasonic endoscope according to claim 7, further comprising:
    a balloon arranged around the ultrasonic probe; and
    a fluid channel, passing through the second circumferential area, for fluid communication to the balloon.

11. The ultrasonic endoscope according to claim 7, wherein a circumferential length of the second circumferential area is larger than a circumferential length of a clearance between adjacent ones of the flexible substrates within the forward end portion body.

12. The radial scan, forward viewing ultrasonic endoscope according to claim 1, wherein said flexible substrates are arranged in arcs around the longitudinal axis of said ultrasonic probe, and a rotation preventing member for preventing relative rotation of said ultrasonic probe and said front end portion body around the longitudinal axis is provided in a position in that area of a circumferential extension of the series of arcs where no flexible substrate is provided.

13. The radial scan, forward viewing ultrasonic endoscope according to claim 12, wherein at least one area of said flexible substrate passage hole is divided into portions in a circumferential direction.

14. The radial scan, forward viewing ultrasonic endoscope according to claim 12, wherein a nut member for urging and fixing said ultrasonic probe against said front end portion body from the front meshes with the outer circumferential surface of the distal end portion of said front end portion body.

15. The radial scan, forward viewing ultrasonic endoscope according to claim 12, wherein said rotation preventing member is independent of both said ultrasonic probe and said front end portion body, and a groove into which said rotation preventing member is to be fitted is formed in each of said ultrasonic probe and said tip body.

16. The radial scan, forward viewing ultrasonic endoscope according to claim 6, wherein the front end portion body has an arcuate groove through which the flexible substrates pass.

17. The radial scan, forward viewing ultrasonic endoscope according to claim 6, wherein a rotation preventing member for preventing relative rotation between the front end portion body and the ultrasonic probe is provided in the circumferential area where no flexible substrate is provided.

18. The radial scan, forward viewing ultrasonic endoscope according to claim 6, wherein a circumferential length of the circumferential area where no flexible substrate is provided is larger than a circumferential length of a clearance between adjacent ones of the flexible substrates within the front end portion body.

* * * * *